United States Patent [19]

Frankenreiter et al.

[11] Patent Number: 5,404,878

[45] Date of Patent: Apr. 11, 1995

[54] METHOD AND APPARATUS FOR AUTOMATIC NON-INVASIVE MONITORING OF A PATIENT'S BLOOD PRESSURE

[75] Inventors: Michael Frankenreiter, Sindelfingen; Gerhard Goebl, Aidlingen, both of Germany

[73] Assignee: Hewlett-Packard Company, Palo Alto, Calif.

[21] Appl. No.: 208,444

[22] Filed: Mar. 9, 1994

Related U.S. Application Data

[63] Continuation-in-part of Ser. No. 6,385, Jan. 19, 1993, abandoned.

[51] Int. Cl.6 .............................................. A61B 5/00
[52] U.S. Cl. .................................... 128/680; 128/681; 128/682; 364/413.03
[58] Field of Search ............................... 128/677–686; 364/413.03

[56] References Cited

U.S. PATENT DOCUMENTS

| | | | |
|---|---|---|---|
| 4,461,266 | 7/1984 | Hood, Jr. | 128/681 |
| 4,796,184 | 1/1989 | Bahr et al. | 128/681 |
| 5,253,648 | 10/1993 | Walloch | 128/681 |

Primary Examiner—Lee S. Cohen
Assistant Examiner—Robert L. Nasser, Jr.

[57] ABSTRACT

In a method for automatic non-invasive monitoring of a patient's blood pressure, a cuff is applied around an arm of the patient and inflated to a predetermined pressure. Thereafter the pressure applied to said cuff is stepwise reduced. On the basis of the amplitudes or peak-to-peak values of the oscillations of the pressure signal measured at the individual pressure steps, a blood pressure value is derived. In order to be able to take arrhythmias into consideration in such a measurement method, oscillations that have been recognized to be artifact-free are sorted in accordance with various criteria, whereupon the frequency is determined with which the oscillations fulfill these criteria. Depending on the frequency with which the criteria are fulfilled, specific oscillations are selected whose mean value is utilized for determining the blood pressure.

25 Claims, 7 Drawing Sheets

THRESHOLD CRITERIA FOR PRESSURE STEP OSCILLATIONS

METHOD AND APPARATUS FOR AUTOMATIC NON-INVASIVE MONITORING OF A PATIENT'S BLOOD PRESSURE

This is a continuation-in-part of application Ser. No. 08/006,385, filed on Jan. 19, 1993, now abandoned.

CROSS REFERENCE TO RELATED APPLICATIONS (1) U.S. patent application, Ser. No. 08/208,448, Entitled: "METHOD AND APPARATUS FOR AUTOMATIC NON-INVASIVE MONITORING OF A PATIENT'S BLOOD PRESSURE", Frankenreiter, M. Attorney Docket: 20-92-015CIP1)

(2) U.S. patent application, Ser. No. 08/208,447, Entitled: "METHOD AND APPARATUS FOR AUTOMATIC NON-INVASIVE MONITORING OF A PATIENT'S BLOOD PRESSURE", Frankenreiter, M. Attorney Docket: 20-92-015-CIP2

FIELD OF THE INVENTION

The present invention relates in general to automatic noninvasive monitoring of a patient's blood pressure. In particular the invention relates to a method for automatic noninvasive monitoring of a patient's blood pressure, comprising the steps of applying a cuff around an arm of the patient, inflating said cuff to a predetermined pressure, generating a pressure signal by means of a pressure sensor, stepwise reducing the pressure applied to said cuff for instance by opening a controllable valve, with the applied pressure being held constant at each step until at least one oscillation caused by a heartbeat has occurred in said pressure signal or until a predetermined time period has expired starting as of holding the applied pressure constant, and the systolic or the diastolic or the mean blood pressure being derived from the amplitudes of the oscillations at the various pressure steps.

DESCRIPTION OF THE PRIOR ART

In a manual method of measuring a patient's blood pressure in non-invasive manner, a cuff is applied to an arm of the patient and pumped up to a blood pressure above the systolic blood pressure of the patient. The arteries of the patient are thereby pressed together in occluding manner. The cuff pressure is then continuously decreased while the physician or the nurse monitors by means of a stethoscope the start and the end of the opening of the arteries in order to determine on the basis of these so-called Korotkoff sounds the upper, systolic and the lower, diastolic blood pressure by simultaneously reading these values off from a manometer.

There are also automatic methods for performing this measurement, called "auscultation technique". The blood pressure monitors employing this technique are not deemed reliable.

Blood pressure monitors and blood pressure measuring methods, respectively, have been employed for a number of years in which the so-called oscillometric method is utilized which uses the oscillations or fluctuations of the walls of the arteries which occur in synchronism with the blood pulse. According to the oscillometric technique, the cuff is pumped up to a pressure beyond the systolic pressure and is then deflated in discrete steps. Alternatively, the cuff is inflated in discrete pressure steps up to a predetermined measure beyond the systolic pressure.

During each step, where the cuff pressure is held substantially constant, a pressure sensor detects the oscillations caused by movement of the arterial walls and superimposed on the constant cuff pressure. The amplitudes of these oscillations are recorded. The oscillations, at the systolic or diastolic pressure, respectively, have an amplitude value or peak-to-peak value that is a fixed percentage of the maximum amplitude or maximum peak-to-peak value at mean pressure. Thus, in the oscillometric measuring method the pressure determined as systolic or diastolic pressure generally is the pressure at which the amplitude or peak-to-peak value of the oscillations is a specific percentage of the maximum amplitude of the oscillations.

Blood pressure monitors employing the aforedescribed oscillometric technique have been known for some time so that it is sufficient for disclosing details of this measurement technique to make reference to the following publications as prior art: U.S. Pat. No. 4,349,034, EP-A-208520, EP-A-353315, EP-A-353316, and U.S. Pat. No. 4,074,711.

U.S. Pat. No. 4,625,277, EP-A-249243 and EP-A-379996 disclose methods and apparatuses for the automative non-invasive monitoring of a patient's blood pressure which do not inflate or deflate the cuff in discrete pressure steps. Rather, in accordance with these prior art methods, the cuff is either continuously inflated to a predetermined pressure while taking the number of pressure signal examples during the course of the continuous inflation of the cuff to then deflate the cuff after having reached the predetermined pressure value, or the cuff is rapidly inflated to the predetermined pressure value and then continuously deflated while taking the pressure signal samples during the course of the continuous deflating of the cuff from the above pressure. Thus, the above-described oscillometric measuring method for determining a patient's blood pressure can be used in both cases, in case of a method taking samples of the pressure signal when holding the applied pressure constant until a heartbeat has occurred, as well as in case of a method taking samples of the pressure signal during the course of the continuously inflating or deflating of the cuff.

However, the pressure signal obtained for example by means of a pressure sensor in the cuff on the patient's arm is not only determined by the static cuff pressure and the described oscillations which are determined by oscillations of the arterial walls due to the blood pressure. In other words, the pressure signal has various disturbance variables superimposed thereon that may have different causes. Typical disturbances superimposed on the pressure signal are movements of the patient and muscular tremor occurring in particular in case of undercooling of the patient. In addition thereto there are physiological peculiarities, including all kinds of arrhythmia, such as for instance bigeminy and trigeminy, as well as the so-called respiratory superimposition, i.e. the superimposition of a signal component caused by the patient's breathing on the useful signal. While movements and muscular tremor must be separated from the measuring signal proper, arrhythmias and respiratory superimpositions are signals to be taken into consideration in the measurement.

It is known in oscillometric blood pressure monitors to disregard such oscillations for determining the blood pressure value which are recognized to have been caused by an artifact or have an artifact superimposed thereon. An artifact in known blood pressure monitors is recognized on the basis of a criterion derived from the so-called oscillation channel. In oscillometric blood pressure monitors, the oscillation channel is understood to be a signal channel obtained on the basis of the so-called pressure channel signal, which constitutes the pressure sensor output, by high-pass filtering. This oscillation channel thus corresponds to the harmonic waves or oscillations superimposed on the pressure channel, disregarding the constant component. This oscillation channel signal is rejected as having an artifact superimposed thereon when either the ascending slope of an oscillation exceeds a maximum increase value or when, at a pressure step, the amplitude difference of two adjacent oscillations exceeds a maximum value or when an envelope criterion is not fulfilled according to which an examination is made as to whether two oscillation amplitudes have not become more than double or less than half between two adjacent steps or when the time interval between two oscillations varies by more than a specific percentage of the average time interval. This examination in the prior art, which is carried out on the basis of the oscillation channel, is not capable of making a distinction whether one of the artifact examination criteria has shown responsive because an artifact was actually present or because an arrhythmia or respiratory superimposition of a greater extent has occurred.

Because of the susceptibility of the algorithm used in the known oscillometric blood pressure monitor, both erroneous measurements and unnecessary alarms occur. This is of significance in particular since such blood pressure monitors are often employed in operating rooms where a multiplicity of other parameters of a patient must also be monitored, which may all cause alarms. Such medical apparatus must therefore keep the number of false alarms as low as possible, however without risking the recognition of a genuine physiological alarm.

SUMMARY OF THE INVENTION

On the basis of this prior art, it is a major object of the present invention to provide a method and an apparatus for automatic non-invasive monitoring of a patient's blood pressure, through which, also in case of arrhythmias, the determination of the systolic and/or diastolic and/or mean blood pressure value is ensured with high accuracy.

As regards the method, this object is met according to a first aspect of the invention by a method for automatic non-invasive monitoring of a patient's blood pressure, comprising the following steps:
  applying a cuff around an arm of the patient,
  inflating said cuff to a predetermined pressure,
  generating a pressure signal,
  stepwise reducing the pressure applied to said cuff,
  holding the applied pressure constant at each step until
    at least one oscillation caused by a heartbeat has occurred in said pressure signal, or until
    a predetermined time period has expired,
  determining whether an instantaneous oscillation fulfills an artifact disturbance criterion, and
  if this condition is fulfilled, disregarding the instantaneous oscillation of the pressure signal in further processing of said signal; or
  if this condition is not fulfilled, sorting the oscillations of the pressure signal, which have now been recognized to be artifact-free, according to at least one of the following three examination criteria a), b) and c):
    a) oscillations having substantially the same amplitudes;
    b) oscillations having substantially the same heart rate;
    c) oscillations fulfilling an envelope criterion;
  determining the number of times or the frequencies of fulfilling the respective criterion a), b) or c),
  examining whether the respective number of times or the frequencies with which the oscillations fulfill criterion a) and/or b) and/or c) exceed predetermined thresholds for fulfilling one criterion each or for fulfilling specific combinations of the criteria,
  if this condition is not fulfilled, detecting at least one further oscillation and jumping back to the step of determining whether the instantaneous oscillation fulfills the artifact disturbance criterion;
  if this condition is fulfilled, calculating an averaged oscillation from the oscillations fulfilling criterion a) and/or b) and/or c) when the frequency thresholds are exceeded, and
  processing the averaged oscillation for determining the systolic and/or diastolic and/or mean blood pressure.

As regards the method, this object is met according to a second aspect of the invention by a method for automatic non-invasive monitoring of a patient's blood pressure, comprising the following steps:
  applying a cuff around an arm of the patient,
  stepwise inflating said cuff to a predetermined pressure and holding the applied pressure constant at each step until
    at least one oscillation caused by a heartbeat has occurred in said pressure signal, or until
    a predetermined time period has expired,
  generating a pressure signal,
  determining whether an instantaneous oscillation fulfills an artifact disturbance criterion, and
  if this condition is fulfilled, disregarding the instantaneous oscillation of the pressure signal in further processing of said signal; or
  if this condition is not fulfilled, sorting the oscillations of the pressure signal, which have now been recognized to be artifact-free, according to at least one of the following three examination criteria a), b) and c):
    a) oscillations having substantially the same amplitudes;
    b) oscillations having substantially the same heart rate;
    c) oscillations fulfilling an envelope criterion;
  determining the number of times or the frequencies of fulfilling the respective criterion a), b) or c),
  examining whether the respective number of times or the frequencies with which the oscillations fulfill criterion a) and/or b) and/or c) exceed predetermined thresholds for fulfilling one criterion each or for fulfilling specific combinations of the criteria,
  if this condition is not fulfilled, detecting at least one further oscillation and jumping back to the step of determining whether the instantaneous oscillation fulfills the artifact disturbance criterion;
  if this condition is fulfilled, calculating an averaged oscillation from the oscillations fulfilling criterion a) and/or b) and/or c) when the frequency thresholds are exceeded, and processing the averaged oscillation for determining the systolic and/or diastolic and/or mean blood pressure, and after having reached the predetermined pressure, deflating said cuff.

As regards the method, this object is met according to a third aspect of the invention by a method for automatic non-invasive monitoring of a patient's blood pressure, comprising the following steps:

applying a cuff around an arm of the patient, continuously inflating said cuff to a predetermined pressure or continuously deflating said cuff from a predetermined pressure, generating a pressure signal during the course of the continuous inflating said cuff to said predetermined pressure or during the course of the continuous deflating said cuff from said predetermined pressure, determining whether an instantaneous oscillation fulfills an artifact disturbance criterion, and if this condition is fulfilled, disregarding the instantaneous oscillation of the pressure signal in further processing of said signal; or if this condition is not fulfilled, sorting the oscillations of the pressure signal, which have now been recognized to be artifact-free, according to at least one of the following three examination criteria a), b) and c):

a) oscillations having substantially the same amplitudes;
   b) oscillations having substantially the same heart rate;
   c) oscillations fulfilling an envelope criterion;

determining the number of times or the frequencies of fulfilling the respective criterion a), b) or c), examining whether the respective number of times or the frequencies with which the oscillations fulfill criterion a) and/or b) and/or c) exceed predetermined thresholds for fulfilling one criterion each or for fulfilling specific combinations of the criteria, if this condition is not fulfilled, detecting at least one further oscillation and jumping back to the step of determining whether the instantaneous oscillation fulfills the artifact disturbance criterion;

if this condition is fulfilled, calculating an averaged oscillation from the oscillations fulfilling criterion a) and/or b) and/or c) when the frequency thresholds are exceeded, and processing the averaged oscillation for determining the systolic and/or diastolic and/or mean blood pressure.

As regards the apparatus, this object is met according to a fourth aspect of the invention by a blood pressure measuring apparatus for automatic noninvasive monitoring of a patient's blood pressure, comprising:

a cuff applied to an arm of the patient, a pump means for inflating said cuff to a predetermined pressure, a pressure sensor for producing a pressure signal, a valve control means for a valve means for stepwise reducing the pressure applied to said cuff and for holding the applied pressure constant at each step until at least one oscillation caused by a heartbeat has occurred in the pressure signal, or until
   a predetermined period of time has expired, an artifact detecting means for determining whether an instantaneous oscillation fulfills an artifact disturbance criterion, and if this condition is fulfilled, disregarding the instantaneous oscillation of the pressure signal in further processing thereof; or if this condition is not fulfilled, sorting the oscillations of the pressure signal, which have now been recognized to be artifact-free, according to at least one of the following three examination criteria a), b) and c):

a) oscillations having substantially the same amplitudes;
   b) oscillations having substantially the same heart rate;
   c) oscillations fulfilling an envelope criterion;

a means for determining the number of times or the frequencies of fulfilling respective criterion a), b) or c), an examination means for examining whether the respective number of times or the frequency with which the oscillations fulfill criterion a) and/or b) and/or c) exceeds predetermined thresholds for fulfilling one criterion each or for fulfilling specific combinations of the criteria, a means for causing detection of at least one further oscillation responsive to the non-fulfillment of this condition, which is fed to said artifact detection means for determining whether the instantaneous oscillation fulfills the artifact disturbance criterion, an oscillation averaging means responsive to fulfillment of said condition, for calculating an averaged oscillation from the oscillations fulfilling said criterion a) and/or b) and/or c) when the frequency thresholds are exceeded, and a processing means for processing the averaged oscillations for determining the systolic and/or the diastolic and/or the mean blood pressure.

As regards the apparatus, this object is met according to a fifth aspect of the invention by a blood pressure measuring apparatus for automatic noninvasive monitoring of a patient's blood pressure, comprising:

a cuff applied to an arm of the patient, a pressure sensor for producing a pressure signal, a pump means for stepwise inflating said cuff to a predetermined pressure and for holding the applied pressure constant at each step until at least one oscillation caused by a heartbeat has occurred in the pressure signal, or until
   a predetermined period of time has expired, an artifact detecting means for determining whether an instantaneous oscillation fulfills an artifact disturbance criterion, and if this condition is fulfilled, disregarding the instantaneous oscillation of the pressure signal in further processing thereof; or if this condition is not fulfilled, sorting the oscillations of the pressure signal, which have now been recognized to be artifact-free, according to at least one of the following three examination criteria a), b) and c):

a) oscillations having substantially the same amplitudes;
   b) oscillations having substantially the same heart rate;
   c) oscillations fulfilling an envelope criterion;

a means for determining the number of times or the frequencies of fulfilling respective criterion a), b) or c), an examination means for examining whether the respective number of times or the frequency with which the oscillations fulfill criterion a) and/or b) and/or c) exceeds predetermined thresholds for fulfilling one criterion each or for fulfilling specific combinations of the criteria, a means for causing detection of at least one further oscillation responsive to the non-fulfillment of this condition, which is fed to said artifact detection means for determining whether the instantaneous oscillation fulfills the artifact disturbance criterion, an oscillation averaging means responsive to fulfillment of said condition, for calculating an averaged oscillation from the oscillations fulfilling said criterion a) and/or b) and/or c) when the frequency thresholds are exceeded, and a processing means for processing the averaged oscillations for determining the systolic and/or the diastolic and/or the mean blood pressure, and a valve means for deflating said cuff when the pressure applied to the cuff has reached the predetermined pressure.

As regards the apparatus, this object is met according to a sixth aspect of the invention by a blood pressure measuring apparatus for automatic noninvasive monitoring of a patient's blood pressure, comprising:

a cuff applied to an arm of the patient, a pump means for continuously inflating said cuff to a predetermined pressure, a pressure sensor for producing a pressure signal during the course of continuously inflating said cuff to said predetermined pressure, an artifact detecting means for determining whether an instantaneous oscillation fulfills an artifact disturbance criterion, and if this condition is fulfilled, disregarding the instantaneous oscillation of the pressure signal in further processing thereof; or if this condition is not fulfilled, sorting the oscillations of the pressure signal, which have now been recognized to be artifact-free, according to at least one of the following three examination criteria a), b) and c):

a) oscillations having substantially the same amplitudes;

b) oscillations having substantially the same heart rate;

c) oscillations fulfilling an envelope criterion;

a means for determining the number of times or the frequencies of fulfilling respective criterion a), b) or c), an examination means for examining whether the respective number of times or the frequency with which the oscillations fulfill criterion a) and/or b) and/or c) exceeds predetermined thresholds for fulfilling one criterion each or for fulfilling specific combinations of the criteria, a means for causing detection of at least one further oscillation responsive to the non-fulfillment of this condition, which is fed to said artifact detection means for determining whether the instantaneous oscillation fulfills the artifact disturbance criterion, an oscillation averaging means responsive to fulfillment of said condition, for calculating an averaged oscillation from the oscillations fulfilling said criterion a) and/or b) and/or c) when the frequency thresholds are exceeded, and a processing means for processing the averaged oscillations for determining the systolic and/or the diastolic and/or the mean blood pressure, and a valve means for deflating said cuff when the pressure applied to the cuff has reached the predetermined pressure.

As regards the apparatus, this object is met according to a seventh aspect of the invention by a blood pressure measuring apparatus for automatic noninvasive monitoring of a patient's blood pressure, comprising:

a cuff applied to an arm of the patient, a pump means for inflating said cuff to a predetermined pressure, valve means for continuously deflating said cuff from said predetermined pressure, a pressure sensor for producing a pressure signal during the course of continuously deflating said cuff from said predetermined pressure, an artifact detecting means for determining whether an instantaneous oscillation fulfills an artifact disturbance criterion, and if this condition is fulfilled, disregarding the instantaneous oscillation of the pressure signal in further processing thereof; or if this condition is not fulfilled, sorting the oscillations of the pressure signal, which have now been recognized to be artifact-free, according to at least one of the following three examination criteria a), b) and c):

a) oscillations having substantially the same amplitudes;

b) oscillations having substantially the same heart rate;

c) oscillations fulfilling an envelope criterion;

a means for determining the number of times or the frequencies of fulfilling respective criterion a), b) or c), an examination means for examining whether the respective number of times or the frequency with which the oscillations fulfill criterion a) and/or b) and/or c) exceeds predetermined thresholds for fulfilling one criterion each or for fulfilling specific combinations of the criteria, a means for causing detection of at least one further oscillation responsive to the non-fulfillment of this condition, which is fed to said artifact detection means for determining whether the instantaneous oscillation fulfills the artifact disturbance criterion, an oscillation averaging means responsive to fulfillment of said condition, for calculating an averaged oscillation from the oscillations fulfilling said criterion a) and/or b) and/or c) when the frequency thresholds are exceeded, and a processing means for processing the averaged oscillations for determining the systolic and/or the diastolic and/or the mean blood pressure.

The invention is based on the finding that, after the pressure signal has been freed from disturbances caused by artifacts, a reliable evaluation of the blood pressure is possible, also in case possible arrhythmias due to specific physiological characteristics of the patient are not known, when the oscillations recognized to be artifact-free are first sorted with respect to oscillations having substantially the same amplitudes and/or oscillations having substantially the same heart rate and/or oscillations fulfilling an envelope criterion. Thereafter, a determination of the frequencies takes place with which the particular criterion is fulfilled. On the basis of the frequencies with which one or two or three of the criteria are fulfilled, it is either established that the instantaneous signal cannot yet be evaluated, in which case a further oscillation is detected. In case the examination of the frequencies with which the oscillations fulfill the criteria, exceeds predetermined thresholds, the thus selected oscillations are averaged and are passed on to blood pressure evaluation for calculating the systolic and/or diastolic and/or mean blood pressure.

DESCRIPTION OF PREFERRED EMBODIMENTS OF THE INVENTION

Figure 1:
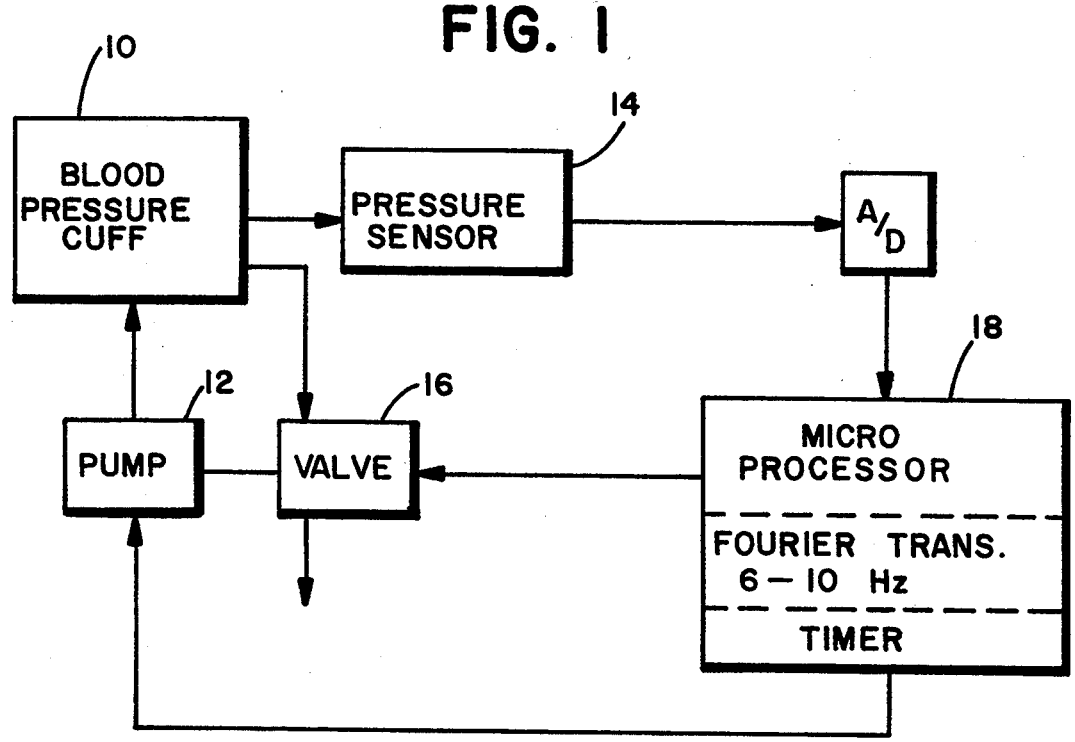
FIG. 1 is a block diagram of a blood pressure measuring system embodying the invention.

The blood pressure measurement apparatus for automatic non-invasive monitoring of a patient's blood pressure is shown in FIG. 1 and comprises a cuff 10 applied to an arm of the patient, a pump 12 for inflating cuff 10 to a predetermined pressure, a pressure sensor 14 for producing a pressure signal, a valve means 16 driven by a microprocessor 18 for stepwise reducing the pressure applied to cuff 10 and for holding the applied pressure constant at each step until either at least one oscillation caused by a heartbeat has occurred in the pressure signal or until a predetermined period of time has expired. Microprocessor 18 determines the systolic or the diastolic or the mean blood pressure on the basis of amplitude relationships of the oscillations at the various pressure steps. Preferably, the systolic and the diastolic blood pressure is determined to be the pressure at which the peak-to-peak value of the oscillation reaches a predetermined percentage (e.g. 60%), of the maximum peak-to-peak value at mean blood pressure.

Figure 2:
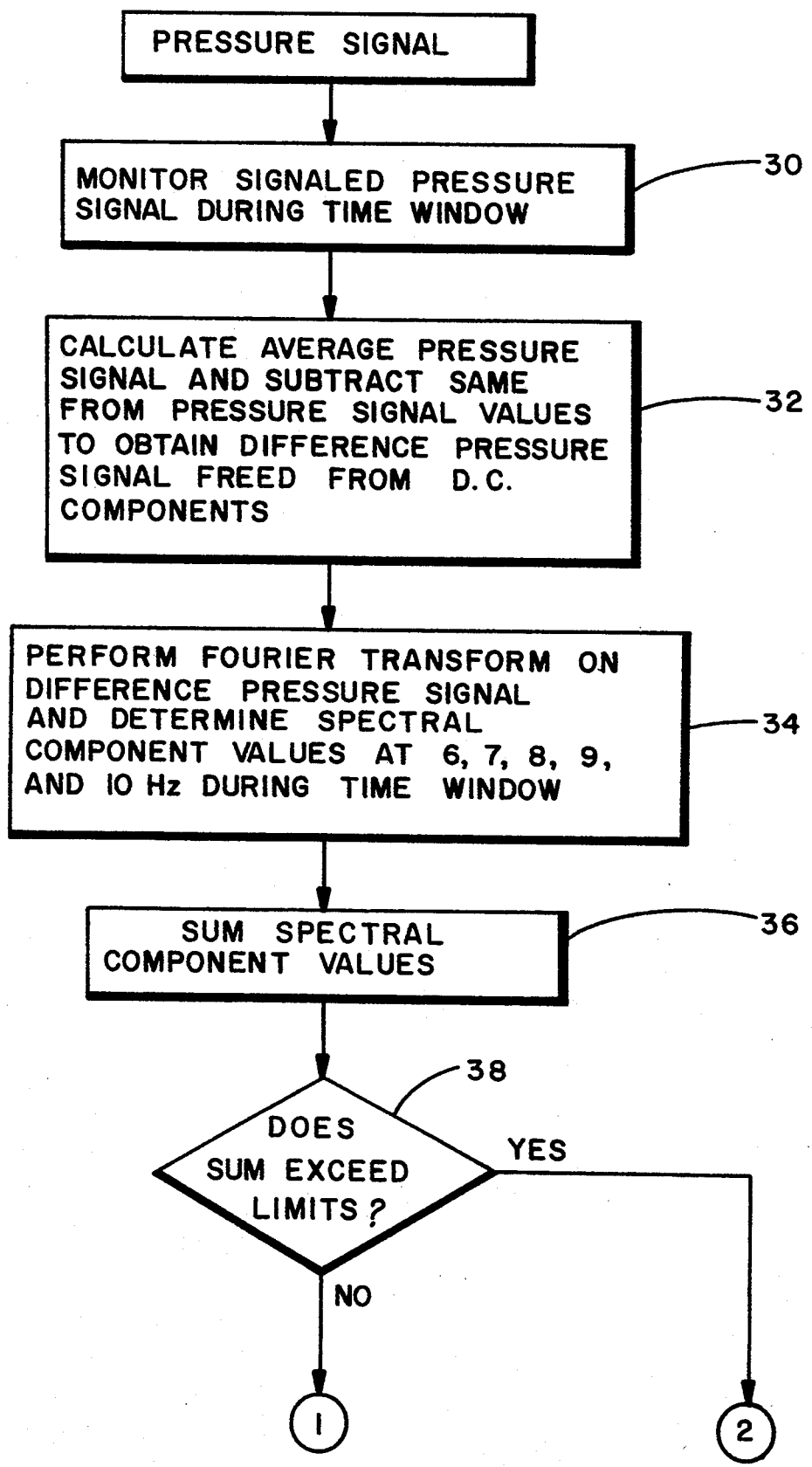
FIG. 2 is a high level logic flow diagram illustrating a method for artifact determination performed by the system of FIG. 1.

Referring to the flow diagram shown in FIG. 2, a pressure channel signal, i.e. a signal produced by pressure sensor 14, which is not high-pass filtered, is monitored during a time window (box 30). The average pressure value is then calculated and subtracted from the pressure signal values to obtain difference pressure values free of any dc or constant pressure component (box 32). The difference pressure values are then subjected to a discrete Fourier transform in the range between 6 and 10 Hz (box 34). Preferably, the values of the discrete frequency components at 6, 7, 8, 9 and 10 Hz are determined.

The discrete Fourier transform turns out to be particularly simple when values (sine/cosine) multiplied by a factor 100 are stored before as integers in a table of the microprocessor. The pressure signal is determined for the discrete Fourier transform within a time window between 0.2 and 5 seconds, preferably within a time window of 1 second, with the average value of the signal across the time window being deducted from the signal to achieve the difference pressure signal (box 32) before the discrete Fourier transform is carried out.

The values of the spectral components of the signal at the frequencies of 6 Hz, 7 Hz, 8 Hz, 9 Hz and 10 Hz are added (box 36). The total sum of the frequency components at these frequencies is compared with a limit value (decision box 38).

When the calculated value of these spectral components of the pressure signal for the frequencies of 6, 7, 8, 9 and 10 Hz exceed a limit value that may be set empirically, this is rated as muscular tremor of the patient (box 40). The instantaneously examined oscillation rated as having a muscular tremor of the patient super- imposed thereon or as being caused by muscular tremor of the patient is disregarded or rejected.

Only such oscillations for which the sum of the values of the frequency components at 6, 7, 8, 9 and 10 Hz does not exceed the limit value, are admitted for further processing for determining the systolic, diastolic or mean blood pressure (box 42).

The aspect of the invention described in so far thus relates to the rejection of such oscillations that are impaired by artifacts caused by trembling of the patient or muscular tremor for instance due to undercooling of the patient.

Figure 3:
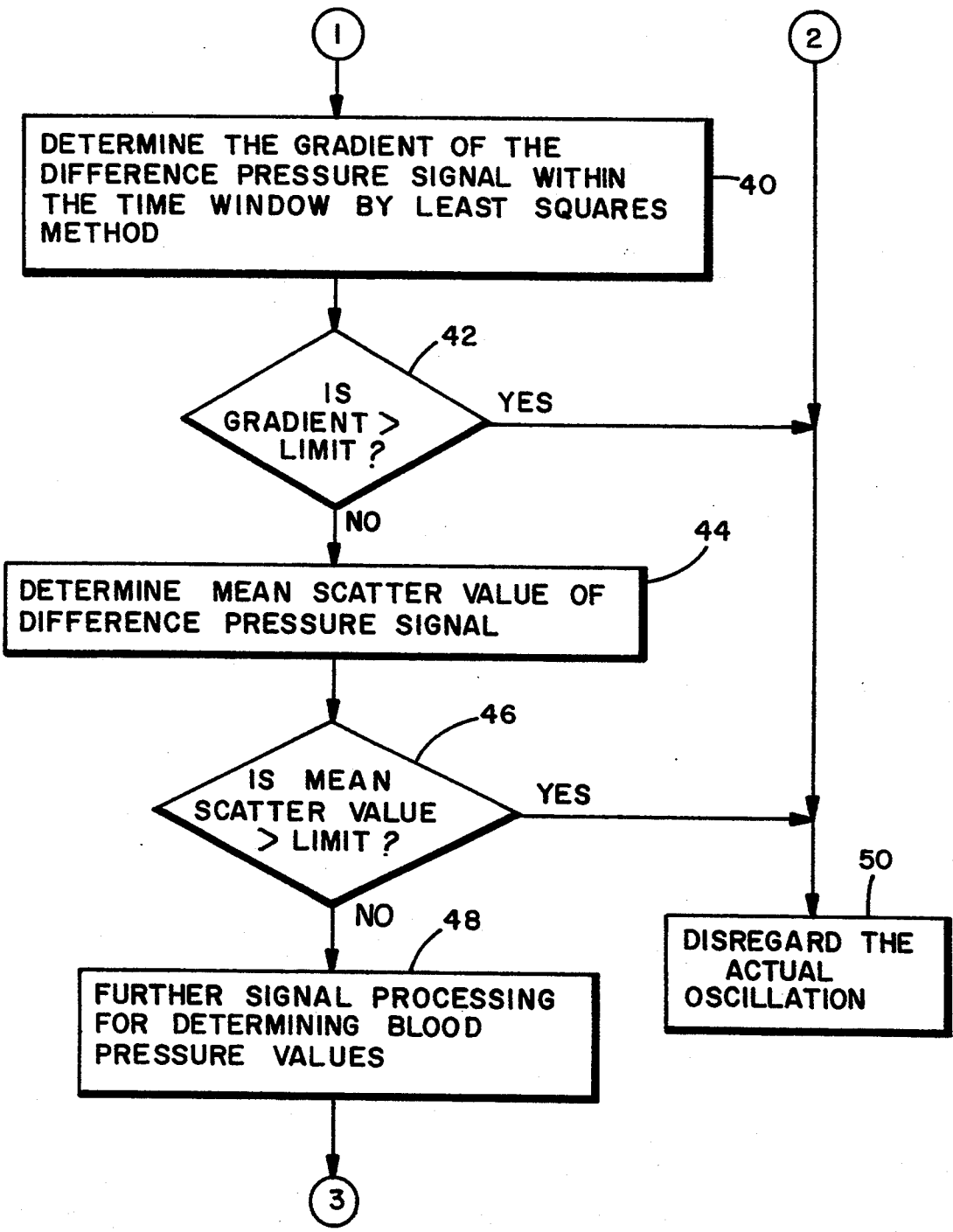
FIG. 3 is a high level logic flow diagram illustrating a further artifact determination method performed by the system of FIG. 1.

As described hereinbefore, artifacts may also be caused by movements of the patient. In order to disregard oscillations that are caused by movements of the patient, additional processing is performed as shown in FIGS. 2 and 3.

Starting again on the basis of the pressure channel signal, a time window is defined by means of a timer within which the pressure channel signal is observed. This timer may be a timer for defining the time window that is also used for the discrete Fourier transform. The time window has a duration between 0.2 and 5 seconds, preferably 1 second. Within the time window (boxes 30, 32), the average value of the pressure channel signal is formed and subtracted from the signal. For determining a gradient of the resulting signal (box 40), which is freed from constant components, a straight line is applied to them signal according to the method of least error squares. Furthermore, the scatter of the signal within the time window is ascertained. In ascertaining the scatter, preferably the mean scatter is calculated, i.e. the mean value of the distance of the particular pressure signal curve point from the mean value thereof (box 44). It is also possible, but not necessary for the purposes of the invention, to calculate a standard deviation according to Gauss.

Thereafter, it is determined (decision boxes 42, 46) whether the gradient and/or the scatter of the pressure channel signal (within the time window) exceed predetermined limit values. If this condition of examination is fulfilled, the conclusion is made that an artifact caused by movement of the patient is present, and the instantaneous oscillation under consideration is rejected or disregarded in further signal processing (box 50).

The evaluation of the remaining oscillations that are not impaired by an artifact is made, as described hereinbefore, by means of algorithms known per se, for deriving the diastolic, systolic or mean blood pressure value from the amplitude values or peak-to-peak values of the oscillations at the individual pressure steps (box 48).

In accordance with the above-described preferred embodiments, the cuff is firstly inflated to the predetermined pressure above the systolic pressure before stepwise reducing the pressure applied to the cuff and holding the pressure constant at each pressure step until either one oscillation caused by the heartbeat has occurred or until a predetermined time period has expired.

The above-described principles of the invention equally apply to a method which derives the pressure samples by stepwise inflating the cuff and holding the pressure constant until at least one oscillation caused by the heartbeat has occurred or until a predetermined time period has expired while generating a pressure signal for this pressure step; i.e. a method which requires the stepwise inflating of the cuff for taking pressure signal samples rather than stepwise deflating the cuff as it has been described with reference to the preferred embodiment.

Similarly, the principles of the invention equally apply to a method for automatic non-invasive monitoring of the patient's blood pressure, wherein the pressure signals are obtained during the course of the continuous inflating of the cuff and/or during the course of the continuous deflating of the cuff.

According to a further aspect of the invention, the pressure signal is processed after it has been found to be free from artifacts (within limits) by one of the two above methods or cumulatively by both methods and in which disturbances due to muscular tremor or movements of the patient are not present. The processing checks for irregularities caused by so-called arrhythmias in such a manner that, in spite of such arrhythmias, a correct evaluation is possible of the patient's blood pressure with respect to systolic and/or diastolic and/or possibly the mean value of the blood pressure.

Figure 4:
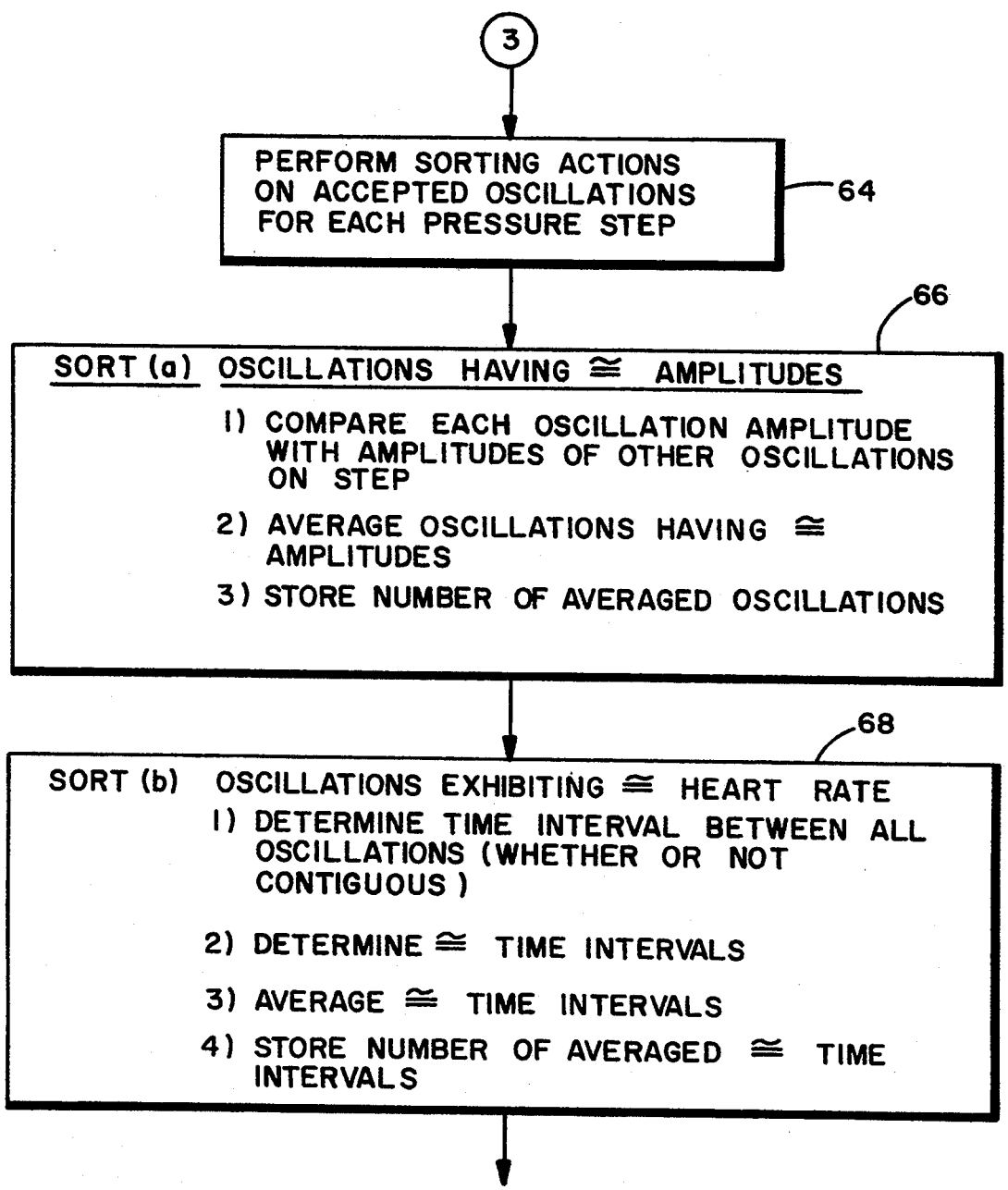
FIGS. 4-6 are high level logic flow diagrams that illustrate pressure signal analysis and sorting actions for determining if signals reach an acceptability threshold.
Figure 5:
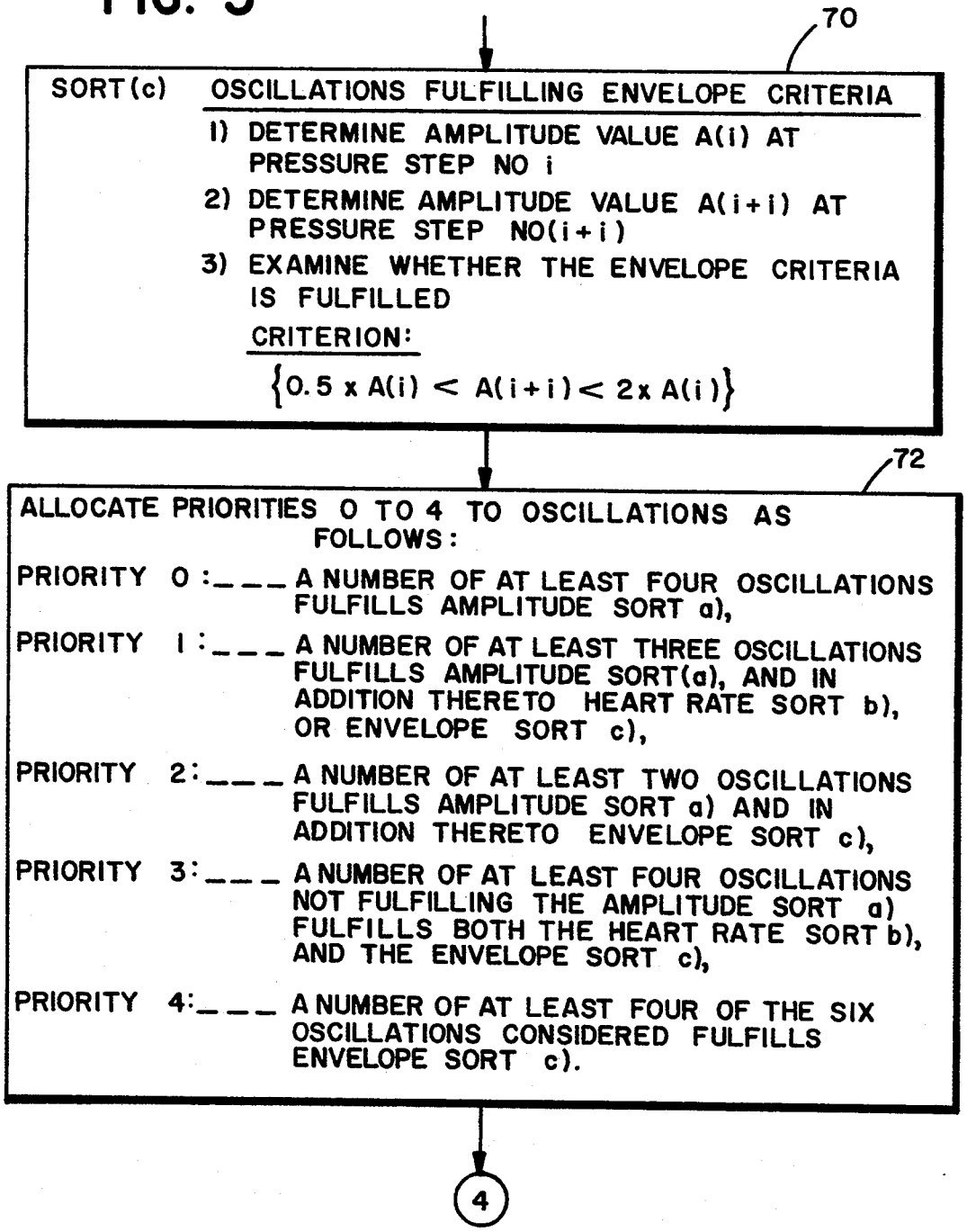

According to this method (see FIGS. 4–6), a first predetermined number of oscillations of the pressure signal (caused by the heartbeat) are detected at a specific pressure step in the course of the stepwise reduction of the pressure applied to the cuff, each of the instantaneous oscillations being subjected to the two afore-described methods of artifact rejection illustrated in FIGS. 2 and 3. As will be hereafter understood from a review of 4, 5a and 5b, oscillations that have been recognized to be artifact-free will then be sorted (box 64) according to at least one of the following criteria a), b), c), namely a) oscillations having substantially the same amplitudes;
b) oscillations having substantially the same heart rate;
c) oscillations fulfilling an envelope criterion.

In examining criterion a) for oscillations having the same amplitude (box 66), all oscillations are compared to each other and those oscillations are averaged which have identical amplitudes within predetermined limits, and the respective number of oscillations from which the average has been calculated is stored as frequency of the oscillations having substantially the same amplitude.

In sorting the oscillations having substantially the same heart rate (box 68) according to criterion b), a determination is made first, of all time intervals between two oscillations each, irrespective of whether or not they follow each other directly. Thereafter, those time intervals are determined which have an identical duration within certain limits. Subsequently, the average is formed of those time intervals that have been recognized to be substantially identical in time. The number of the time intervals from which the average has been taken is then stored as the frequency with which criterion b) is fulfilled.

In sorting the oscillations according to criterion c) (box 70, FIG. 5), the individual oscillations are examined as to whether they fulfill the envelope criterion, i.e, whether successive oscillations (oscillations obtained at two different pressure steps) have not become more than double or less than half (these factors may vary in dependence of the "pressure step width", i.e., the duration of the pressure steps). If the oscillations under comparison differ by more than the double or less than the half, they do not fulfill the envelope criterion. More specifically, the envelope criterion compares the amplitude measured during a pressure step corresponding to a pressure of, for example, 140 mm Hg with an amplitude measured at the preceding pressure step corresponding to a pressure of, for example, 148 mm Hg. For a measurement to be valid, the amplitude measured at the actual pressure step cannot be larger than twice the amplitude measured at the previous pressure step and cannot be smaller than one half of the amplitude of pressure measured at the previous pressure step. Otherwise, the actual amplitude does not fulfill this "envelope criterion".

The average is then formed of the amplitude of the oscillations fulfilling the envelope criterion, and the number of oscillations from which the average has been taken is stored for determining the frequency with which the envelope criterion is fulfilled.

In a specific embodiment of the method according to the invention, a number of at least three, but at the most six oscillations is considered at one pressure step.

After such sorting of the oscillations, an examination is made as to whether the respective frequency with which the oscillations fulfill criterion a) and/or b) and/or c) exceeds predetermined frequency thresholds for fulfilling one criterion each or for fulfilling specific combinations of the criteria.

Figure 6:
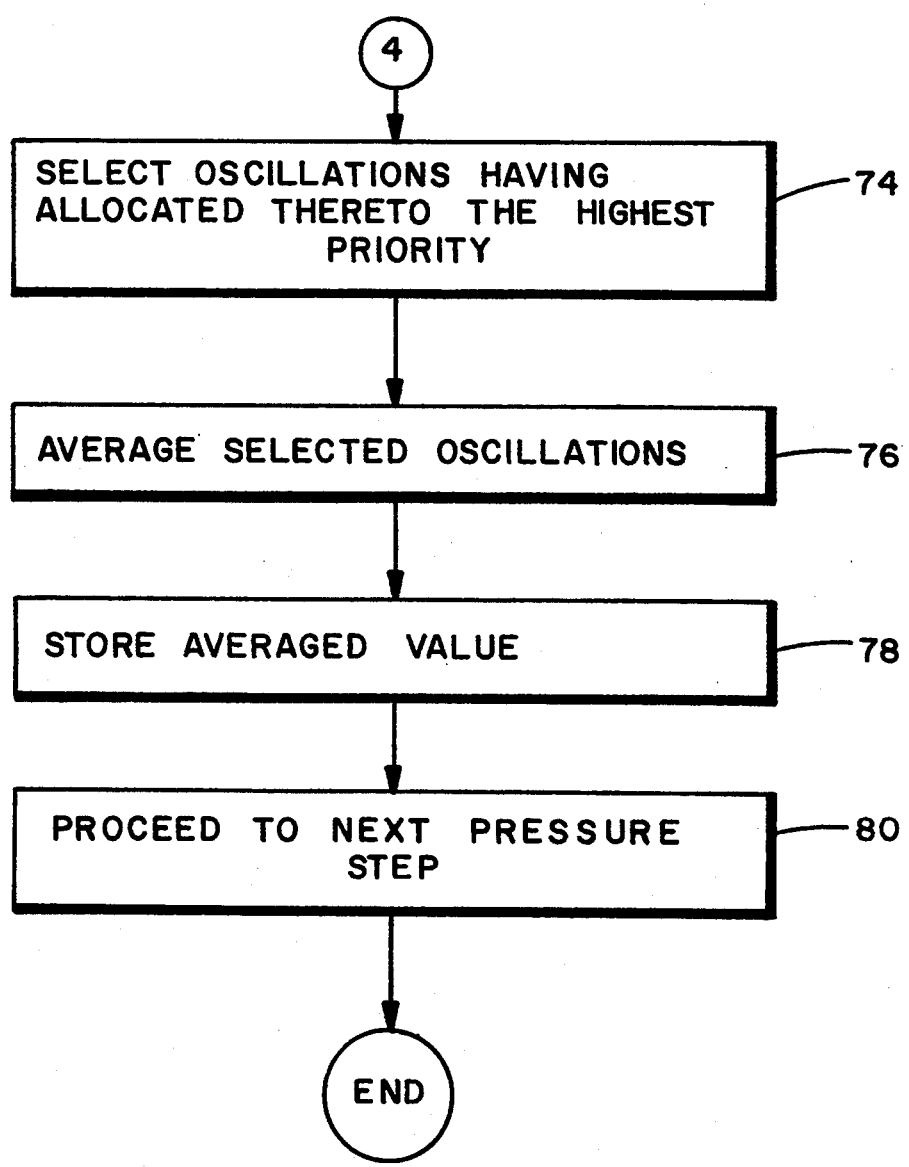
Figure 7:
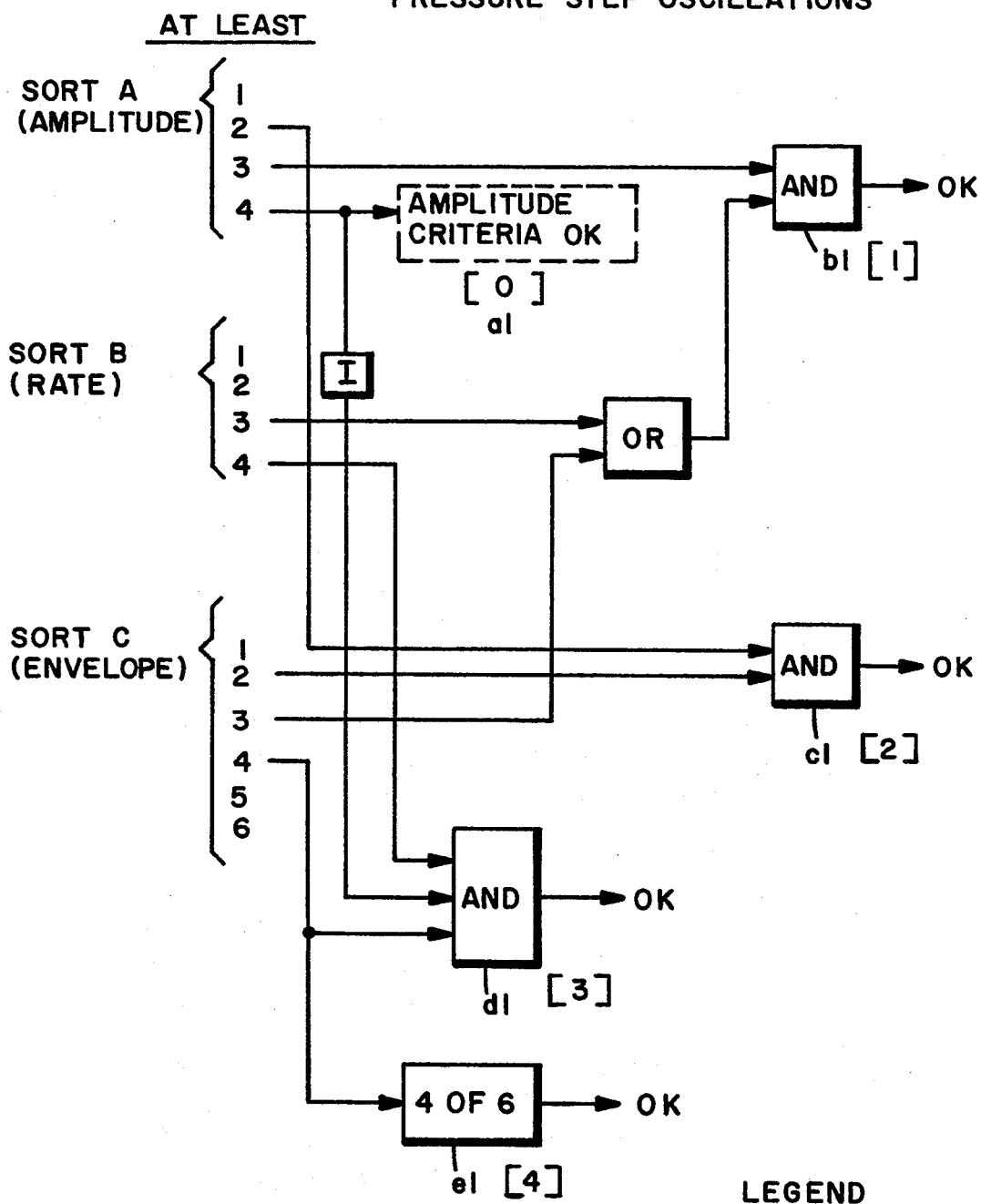
FIG. 7 is a schematic diagram showing the logical threshold criteria used in the acceptability determination.

In a preferred embodiment, this examination comprises an examination of the following criteria a1) to e1) which are illustrated schematically in FIG. 7 and are listed in box 72 in FIG. 6.

a1) a number of at least four oscillations fulfills amplitude criterion a),
b1) a number of at least three oscillations fulfills amplitude criterion a) and in addition thereto heart rate criterion b) or envelope criterion c),
c1) a number of at least two oscillations fulfills amplitude criterion a) and in addition thereto envelope criterion c),
d1) a number of at least four oscillations not fulfilling the amplitude criterion a) fulfills both the heart rate criterion b) and the envelope criterion c),
e1) a number of at least four of the six oscillations considered fulfills envelope criterion c).

Any signal, the oscillations of which fulfill one of the examination criteria a1) to e1), provides sufficient detection safety. A signal whose oscillations do not fulfill any one of the examination criteria a1) to e1) is not considered to permit an evaluation with sufficient reliability. In that case a further oscillation is detected at the pressure step under consideration, whereafter the method, starting from the step of determining whether the instantaneous oscillation fulfills an artifact disturbance criterion, is repeated with this further oscillation which replaces the respective oldest oscillation value on the pressure step. The examination criteria a1), b1), c1), d1), and e1) have priorities 0, 1, 2, 3, 4 associated therewith in the sequence indicated, with the priority 0 being the highest priority (box 72). Those oscillations are selected that fulfill the examination criterion with the highest priority (FIG. 6, box 74).

The thus selected oscillations are averaged (box 76), whereafter the thus determined mean value of the oscillations at this pressure step is stored (box 78).

After all pressure steps have been passed (box 80), the systolic or diastolic or mean blood pressure value is calculated in the described manner, which is known per se, from the thus determined and stored averaged oscillations for the individual pressure steps.

On the basis of the priority associated with the selected oscillations according to the above scheme, it can be derived whether the blood pressure signal under consideration is free from arrhythmias, which is so when the priority=0 is present, or whether the signal concerned displays strong arrhythmias (priority 4).

The method according to the invention renders possible to create a quality indicator for each blood pressure measurement.

To this end, data are stored in a data bank as to whether disturbances and artifacts, respectively, have occurred in the pressure signals examined, of what nature the disturbance is, how long it lasted and whether the patient has physiological peculiarities as derivable from the priorities that give information on arrhythmias.

The signals ascertained, namely the values for heart rate and pulse pressure in relation to specific values of the systole, can each be classified in groups, due to physiological conditions, which are within physiologically likely ranges, within doubtful ranges or within very doubtful or unlikely ranges, since there are conditions in the human physiology which occur with high probability, with little probability and with extremely little probability.

A criterion for this association or classification is the pulse pressure, i.e. the difference between the systolic and diastolic values.

For a maximum pulse pressure, the following rules can be set up:

| | |
|---|---|
| heart rate ≦150 bpm and pulse pressure >70% of systolic value or | doubtful |
| pulse pressure >80% of systolic value or heart rate >150 bpm and | very doubtful |
| pulse pressure >50% of systolic value and pulse pressure >50 mmHg | doubtful |
| pulse pressure >70% of systolic value and pulse pressure >60 mmHg | very doubtful |

For a minimum pulse pressure, the following rules can be set up:

| | | |
|---|---|---|
| heart rate >150 bpm and | | |
| pulse pressure | <15% of systolic value for systole <160 mmHg <20% for systole 160–200 mmHG <25% for systole >200 mmHG | doubtful |
| pulse pressure | <5% for systole <160 mmHg <10% for systole 160–200 mmHG <15% for systole >200 mmHG | very doubtful |
| heart rate 50–150 bpm | | |
| pulse pressure | <18% for systole <160 mmHg <23% for systole 160–200 mmHG <28% for systole >200 mmHG | doubtful |
| pulse pressure | <8% for systole <160 mmHg <13% for systole 160–200 mmHG <18% for systole >200 mmHG | very doubtful |
| heart rate <50 bpm | | |
| pulse pressure | <20% for systole <160 mmHg <25% for systole 160–200 mmHG | doubtful |

-continued

| | | |
|---|---|---|
| pulse pressure | <30% for systole >200 mmHG <10% for systole <160 mmHg <15% for systole 160–200 mmHG <20% for systole >200 mmHG | very doubtful |

For further criteria, the following rules can be set up:

| | |
|---|---|
| diastole >150 mmHG | doubtful |
| diastole >200 mmHG | very doubtful |
| systole >180 mmHG + heart rate >180 bpm | doubtful |
| systole >180 mmHg + heart rate >200 bpm | very doubtful |
| systole <70 mmHg + heart rate <100 bpm | doubtful |
| systole <50 mmHg + heart rate <100 bpm | very doubtful |

On the basis of these two types of input criteria, namely medical aspects and the measurement history, the blood pressure values can easily be classified, e.g. in 5 or 10 classes. The classes relate exclusively to the reliability of the values.

This classification can be made as follows:
Class 1: no disturbances, no arrhythmia, values within expected ranges (normal physiological ranges)
Class 2: no disturbances, arrhythmias, values within expected ranges
Class 3: slight disturbances and/or arrhythmia, values within expected ranges
Class 4: strong disturbances and/or arrhythmia, values doubtful
Class 5: strong disturbances and/or arrhythmia, values very doubtful In other words, the method according to the invention, which at first rejects artifacts and then recognizes conditions with arrhythmias from the oscillations freed from artifacts, renders possible a classification of the blood pressure values ascertained, with these values being dependent on whether the particular signals for determining the blood pressure were free from artifacts, contained slight or strong arrhythmias, were free from arrhythmias or contained slight or strong arrhythmias, respectively, and yielding value correlations between heart rate, blood pressure and systolic blood pressure value which are either likely, unlikely or extremely unlikely on the basis of the physiological conditions.

We claim:

1. A method for use in automatic non-invasive monitoring of a patient's blood pressure, wherein a cuff is applied around an arm of the patient, the cuff is inflated to a predetermined pressure so as to generate a pressure signal from an attached pressure sensor, and a pressure applied to the cuff is step wise reduced, all while monitoring pressure oscillations, the method comprising the steps of:
   (a) holding a cuff pressure constant at each step until a first predetermined number of oscillations caused by the patient's heartbeat has occurred in said pressure signal, or until a predetermined time period has expired,
   (b) determining whether an oscillation fulfills an artifact disturbance criterion, and
   (c) if yes, disregarding the oscillation of the pressure signal and proceeding to a next oscillation signal; or
   (d) if no, sorting the oscillations of the pressure signal, which are recognized as artifact-free, according to at least one of the following examination criteria 1), 2) and 3):
1) oscillations having substantially the same amplitudes;
2) oscillations exhibiting substantially the same heart rate;
3) oscillations fulfilling an envelope criterion;
(e) determining a number for at least one criteria 1, 2 or 3 of oscillations that fulfill said at least one of criteria 1, 2 or 3,
(f) examining whether the respective numbers indicating a fulfillment of criterion 1) and/or 2) and/or 3) exceed predetermined thresholds for fulfilling one each of said criterion or fulfill specific combinations of the criteria,
(g) if examining step (f) is not fulfilled, detecting at least one further oscillation and jumping back to step (b) and repeating steps b–f;
h) if examining step (f) is fulfilled, calculating an averaged oscillation from oscillations that fulfill criterion 1) and/or 2) and/or 3) when the respective fulfillment number thresholds are exceeded, and
(i) storing said averaged oscillation at each of a plurality of pressure steps, and
(j) processing said averaged oscillations for use in determining a systolic and/or a diastolic and/or a mean blood pressure.

2. A method according to claim 1, wherein the step of sorting the oscillations having substantially the same amplitudes (d1) comprises the following partial steps:
comparing amplitudes of all oscillations with each other,
averaging those oscillations that have the same amplitude within predetermined limits, and
storing the respective number of oscillations from which the average has been derived in the form of a number of oscillations having substantially the same amplitude.

3. A method according to claim 1, wherein the step of sorting the oscillations having substantially the same heart rate (d2) comprises the following partial steps:
determining time intervals between all oscillations, irrespective of whether or not the oscillations directly follow each other,
determining those time intervals that have a substantially identical duration, within certain limits,
calculating an average of those time intervals that have been determined to be substantially identical, and
storing the number of the time intervals from which the average has been calculated as an indication of a frequency which the criterion of substantially the same heart rate of the oscillations is fulfilled.

4. A method according to claim 1, wherein the step of sorting the oscillations fulfilling an envelope criterion (d3) comprises the following partial steps:
examining each individual oscillation for fulfillment of an envelope criterion,
averaging the amplitude of those oscillations that fulfill the envelope criterion,
storing the number of oscillations from which the average has been taken as an indication of a frequency with which the envelope criterion is fulfilled.

5. A method according to claim 1, wherein step f comprises an examination whether at least one of the following examination criteria is fulfilled:

a1) a number of at least N1 oscillations fulfills said amplitude criterion 1),
b1) a number of at least N2 oscillations fulfills said amplitude criterion 1) and in addition thereto either said heart rate criterion 1) or said envelope criterion 3),
c1) a number of at least N3 oscillations fulfills said amplitude criterion 1) and in addition thereto said envelope criterion 3),
d1) a number of at least N4 oscillations not fulfilling said amplitude criterion 1) fulfills both said heart rate criterion 2) and said envelope criterion 3),
e1) a number of at least N5 oscillations fulfills said envelope criterion 3).

6. A method according to claim 5, further comprising the step of examining all of said examination criteria a1), b1), c1), d1) and e1),
with the priorities 0, 1, 2, 3 and 4 being associated with said examination criteria a1), b1), c1), d1) and e1), the priority 0 being the highest priority and the priorities indicating the quality of the systolic or diastolic or mean blood pressure determined on the basis of the oscillations averaged for each priority of examination.

7. A method according to claim 5, wherein $N1=4, N2=3, N3=2, N4=4$ and $N5=4$.

8. A method for use in automatic non-invasive monitoring of a patient's blood pressure, wherein a cuff is applied around an arm of the patient, the cuff is inflated to a predetermined pressure so as to generate a pressure signal from an attached pressure sensor, all while monitoring pressure oscillations, the method comprising the steps of:
(a) stepwise inflating said cuff to a predetermined pressure
(b) holding an applied pressure constant at each step until
at least one oscillation caused by a heartbeat has occurred in said pressure signal, or until
a predetermined time period has expired,
(c) determining whether an oscillation fulfills an artifact disturbance criterion, and
(d) if yes, disregarding the oscillation of the pressure signal and proceeding to a next oscillation signal; or
(e) if no, sorting the oscillations of the pressure signal, which have now been recognized to be artifact-free, according to at least one of following three examination criteria 1), 2) and 3):
1) oscillations having substantially the same amplitudes:
2) oscillations having substantially the same heart rate;
3) oscillations fulfilling an envelope criterion;
f) determining a number of time, that the oscillations fulfill said at least one of criteria 1), 2) or 3),
g) examining whether the respective number of times indicating a fulfillment of criterion 1) and/or 2) and/or 3) exceed predetermined thresholds for fulfilling one each of said criterion or fulfill specific combinations of the criteria,
(h) if examining step (g) is not fulfilled, detecting at least one further oscillation and jumping back to the step (c) and repeating steps (d) to (g),
(i) if examining step (g) is fulfilled, calculating an averaged oscillation from the oscillations fulfilling criterion 1) and/or 2) and/or 3) when the respective fulfillment number thresholds are exceeded, and (j) processing the averaged oscillation for use in determining a systolic and/or a diastolic and/or a mean blood pressure, and (k) after having reached the predetermined pressure, deflating said cuff.

9. A method according to claim 8, wherein the step of sorting the oscillations having substantially the same amplitudes (e1) comprises the following partial steps:
comparing amplitudes of all oscillations with each other,
averaging those oscillations that have the same amplitudes within predetermined limits, and
storing the respective number of oscillations from which the average has been taken in the form of the number of oscillations having substantially the same amplitude.

10. A method according to claim 8, wherein the step of sorting the oscillations having substantially the same heart rate (e2) comprises the following partial steps:
determining time intervals between two oscillations each, irrespective of whether or not these directly follow each other,
determining those time intervals that have an identical duration, within certain limits,
calculating an average of those time intervals that have been recognized to be substantially identical, and
storing the number of the time intervals from which the average has been calculated as an indication of a frequency which the criterion of substantially the same heart rate is fulfilled.

11. A method according to claim 8, wherein the step of sorting the oscillations fulfilling an envelope criterion (e3) comprises the following partial steps:
examining each individual oscillation for fulfillment of an envelope criterion,
averaging amplitudes of those oscillations that fulfill the envelope criterion,
storing the number of oscillations from which the average has been taken for determining a frequency with which the envelope criterion is fulfilled.

12. A method according to claim 8, wherein the step of examining (g) comprises the examination of whether at least one of the following examination criteria is fulfilled:
a1) a number of at least N1 oscillations fulfills said amplitude criterion 1),
b1) a number of at least N2 oscillations fulfills said amplitude criterion 1) and in addition thereto either said heart rate criterion 2) or said envelope criterion 3),
c1) a number of at least N3 oscillations fulfills said amplitude criterion 1) and in addition thereto said envelope criterion 3),
d1) a number of at least N4 oscillations not fulfilling said amplitude criterion 1) fulfills both said heart rate criterion 2) and said envelope criterion 3),
e1) a number of at least N5 oscillations fulfills said envelope criterion 3).

13. A method according to claim 12, further comprising the step of examining all of said examination criteria a1), b1), c1), d1), and e1) with the priorities 0, 1, 2, 3 and 4 being associated with said examination criteria a1), b1), c1), d1), and e1), the priority 0 being the highest priority and the priorities indicating the quality of the systolic or diastolic or mean blood pressure determined on the basis of the oscillations averaged for each priority of examination.

14. A method according to claim 12, wherein

N1=4, N2=3, N3=2, N4=4, and N5=4.

15. A method for use in automatic non-invasive monitoring of a patient's blood pressure, wherein a cuff is applied around an arm of the patient, the cuff is inflated to a predetermined pressure so as to generate a pressure signal from an attached pressure sensor, all while monitoring pressure oscillations, the method comprising the steps of:

(a) continuously inflating said cuff to a predetermined pressure or continuously deflating said cuff from a predetermined pressure, (b) wherein the pressure signal is generated during the course of continuously inflating said cuff to said predetermined pressure or during the course of continuously deflating said cuff from said predetermined pressure, (c) determining whether an oscillation fulfills an artifact disturbance criterion, and (d) if yes, disregarding the oscillation of the pressure signal and proceeding to a next oscillation signal; or (e) if no, sorting the oscillations of the pressure signal, which have now been recognized to be artifact-free, according to at least one of the following three examination criteria 1), 2) and 3):
1) oscillations having substantially the same amplitudes;
2) oscillations having substantially the same heart rate;
3) oscillations fulfilling an envelope criterion;

(f) determining a number of times that the oscillations fulfill said at least one of criteria 1), 2) or 3), (g) examining whether the respective number of times indicating a fulfillment of criterion 1), and/or 2) and/or 3) exceed predetermined thresholds for specific combinations of the criteria, fulfilling one each of said criterion or fulfill (h) if examining step (g) is not fulfilled, detecting at least one further oscillation and jumping back to the step (c) and repeating steps (d) to (g), (i) if examining step (g) is fulfilled, calculating an averaged oscillation from the oscillations fulfilling criterion 1) and/or 2) and/or 3) when the respective fulfillment number thresholds are exceeded, and (j) processing the averaged oscillation for use in determining a systolic and/or a diastolic and/or a mean blood pressure.

16. A method according to claim 15, wherein the step of sorting the oscillations having substantially the same amplitudes (e1) comprises the following partial steps:
comparing amplitudes of all oscillations with each other,
averaging those oscillations that have the same amplitudes within predetermined limits, and
storing the respective number of oscillations from which the average has been taken in the form of the number of oscillations having substantially the same amplitude.

17. A method according to claim 15, wherein the step of sorting the oscillations having substantially the same heart rate (e2) comprises the following partial steps:
  determining time intervals between two oscillations each, irrespective of whether or not these directly follow each other,
  determining those time intervals that have an identical duration, within certain limits,
  calculating an average of those time intervals that have been recognized to be substantially identical, and
  storing the number of the time intervals from which the average has been calculated as an indication of a frequency which the criterion of substantially the same heart rate is fulfilled.

18. A method according to claim 15, wherein the step of sorting the oscillations fulfilling an envelope criterion (e3) comprises the following partial steps:
  examining each individual oscillation for fulfillment of an envelope criterion,
  averaging the amplitudes, of those oscillations that fulfill the envelope criterion,
  storing the number of oscillations from which the average has been taken for determining a frequency with which the envelope criterion is fulfilled.

19. A method according to claim 18, wherein the step of examining (g) comprises the examination whether at least one of the following examination criteria is fulfilled:
  a1) a number of at least N1 oscillations fulfills said amplitude criterion 1),
  b1) a number of at least N2 oscillations fulfills said amplitude criterion 1) and in addition thereto either said heart rate criterion 2) or said envelope criterion 3),
  c1) a number of at least N3 oscillations fulfills said amplitude criterion 1) and in addition thereto said envelope criterion 3),
  d1) a number of at least N4 oscillations not fulfilling said amplitude criterion 1) fulfills both said heart rate criterion 2) and said envelope criterion 3),
  e1) a number of at least N5 oscillations fulfills said envelope criterion 3).

20. A method according to claim 19, further comprising the step of examining all of said examination criteria a1), b1), c1), d1), and e1) with the priorities 0, 1, 2, 3, and 4 being associated with said examination criteria a1), b1), c1), d1), and e1), the priority 0 being the highest priority and the priorities indicating the quality of the systolic or diastolic or mean blood pressure determined on the basis of the oscillations averaged for each priority of examination.

21. A method according to claim 19, wherein

N1=4, N2=3, N3=2, N4=4, and N5=4.

22. In a blood pressure measuring apparatus for automatic noninvasive monitoring of a patient's blood pressure, the apparatus employing a blood pressure cuff applied to an arm of the patient, the apparatus comprising:
  pump means for inflating said cuff to a predetermined pressure,
  a pressure sensor for producing a pressure signal,
  valve control means having a valve means for stepwise reducing an applied pressure to said cuff and for holding the applied pressure constant at each step until
    a first predetermined number of oscillations caused by heartbeat has occurred in the pressure signal, or until
    a predetermined period of time has expired,
  artifact detecting means coupled to said pressure sensor for determining whether an instantaneous oscillation of the pressure signal fulfills an artifact disturbance criterion, and if yes, signalling to disregard the instantaneous oscillation of the pressure signal; or
  if no, sorting oscillations of the pressure signal, which are recognized to be artifact-free, according to at least one of the following three examination criteria a), b) and c):
    a) oscillations having substantially the same amplitude;
    b) oscillations exhibiting a substantially same heart rate;
    c) oscillations fulfilling an envelope criterion;
  a means for determining the number of times respective criterion a), b) or c) are fulfilled,
  means for examining whether the respective number of times the oscillations fulfill criterion a) and/or b) and/or c) exceed predetermined thresholds for fulfilling one criterion each or for fulfilling specific combinations of the criteria,
  means for causing detection of at least one further oscillation responsive to no such thresholds being exceeded, said further oscillations fed to said artifact detection means for determining whether the further oscillation fulfills the artifact disturbance criterion,
  oscillation averaging means responsive to a threshold being exceeded, for calculating an averaged oscillation from the oscillations fulfilling said criterion a) and/or b) and/or c) when a respective threshold is exceeded, and
  processing means for processing the averaged oscillations for use in determining a systolic and/or a diastolic and/or a mean blood pressure.

23. In a blood pressure measuring apparatus for automatic noninvasive monitoring of a patient's blood pressure, the apparatus employing a cuff that includes a pressure sensor applied to an arm of the patient, the apparatus comprising:
  pump means for stepwise inflating said cuff to a predetermined applied pressure and for holding the applied pressure constant at each step until
    at least one oscillation caused by a heartbeat has occurred in a pressure signal provided by said pressure sensor, or until
    a predetermined period of time has expired,
  artifact detecting means for determining whether an oscillation fulfills an artifact disturbance criterion, and
  if yes, signalling to disregard the oscillation of the pressure signal; or
  if no, sorting the oscillations of the pressure signal, which have now been recognized to be artifact-free, according to at least one of the following three examination criteria a), b) and c):
    a) oscillations having substantially the same amplitudes;
    b) oscillations exhibiting a substantially heart rate;
    c) oscillations fulfilling an envelope criterion;

means for determining the number of times the criteria a), b) or c) are fulfilled, means for examining whether the respective number of times the oscillations fulfill criterion a) and/or b) and/or c) exceeds predetermined thresholds for fulfilling one each of said criterion or fulfill specific combinations of the criteria, means for causing detection of at least one further oscillation responsive to no such threshold being exceeded said further oscillations ted to said artifact detection means for determining whether the further oscillation fulfills the artifact disturbance criterion, oscillation averaging means responsive to a threshold being exceeded, for calculating an averaged oscillation from the oscillations fulfilling said criterion a) and/or b) and/or c) a respective threshold is exceeded, processing means for processing the averaged oscillations for use in determining a systolic and/or a diastolic and/or a mean blood pressure, and valve means for deflating said cuff when the pressure applied to the cuff has reached the predetermined pressure.

24. In a blood pressure measuring apparatus for automatic noninvasive monitoring of a patient's blood pressure, the apparatus employing a cuff applied to an arm of the patient, the apparatus comprising:

pump means for continuously inflating said cuff to a predetermined pressure, a pressure sensor for producing a pressure signal during the course of continuously inflating said cuff to said predetermined pressure, artifact detecting means coupled to said pressure sensor for determining whether an oscillation fulfills an artifact disturbance criterion, and if yes, signalling to disregard the oscillation of the pressure signal; or if no, sorting the oscillations of the pressure signal, which have now been recognized to be artifact-free, according to at least one of the following three examination criteria a), b) and c):

a) oscillations having substantially the same amplitudes;

oscillations exhibiting a substantially same heart rate;

c) oscillations fulfilling an envelope criterion;

means for determining the number of times the criteria a), b) or c) are fulfilled, means for examining whether the respective number of times the oscillations fulfill criterion a) and/or b) and/or c) exceeds predetermined thresholds for fulfilling one each of said criterion or fulfill specific combinations of the criteria, means for causing detection of at least one further oscillation responsive to no such threshold being exceeded said further oscillations fed to said artifact detection means for determining whether the further oscillation fulfills the artifact disturbance criterion, oscillation averaging means responsive to a threshold being exceeded, for calculating an averaged oscillation from the oscillations fulfilling said criterion a) and/or b) and/or c) a respective threshold is exceeded, processing means for processing the averaged oscillations for use in determining a systolic and/or a diastolic and/or a mean blood pressure, and valve means for deflating said cuff when the pressure applied to the cuff has reached the predetermined pressure.

25. In a blood pressure measuring apparatus for automatic noninvasive monitoring of a patient's blood pressure, the apparatus employing a cuff applied to an arm of the patient, the apparatus comprising;

pump means for inflating said cuff to a predetermined pressure, valve means for continuously deflating said cuff from said predetermined pressure, a pressure sensor for producing a pressure signal during the course of continuously deflating said cuff from said predetermined pressure, artifact detecting means coupled to said pressure sensor for determining whether an oscillation fulfills an artifact disturbance criterion, and if yes, signalling to disregard the oscillation of the pressure signal; or if no, sorting the oscillations of the pressure signal, which have now been recognized to be artifact-free, according to at least one of the following three examination criteria a), b) and c):

a) oscillations having substantially the same amplitudes;

b) oscillations exhibiting a substantially same heart rate;

c) oscillations fulfilling an envelope criterion;

means for determining the number of times the criteria a), b) or c) are fulfilled, means for examining whether the respective member of times the oscillations fulfill criterion a) and/or b) and/or c) exceeds predetermined thresholds for fulfilling one each of said criterion or fulfill specific combinations of the criteria, means for causing detection of at least one further oscillation responsive to no such threshold being exceeded said further oscillations fed to said artifact detection means for determining whether the further oscillation fulfills the artifact disturbance criterion, oscillation averaging means responsive to a threshold being exceeded, for calculating an averaged oscillation from the oscillations fulfilling said criterion a) and/or b) and/or c) a respective threshold is exceeded, and processing means for processing the averaged oscillations for use in determining a systolic and/or a diastolic and/or a mean blood pressure.

* * * * *

UNITED STATES PATENT AND TRADEMARK OFFICE
CERTIFICATE OF CORRECTION

PATENT NO. : 5,404,878
DATED : Apr. 11, 1995
INVENTOR(S) : Frankenreiter et al.

It is certified that error appears in the above-identified patent and that said Letters Patent is hereby corrected as shown below:

In colum 16, line 50, after "of" insert --of--

In column 16, line 57, the word "time" should be replaced by the word --times--.

In column 18, line 44, the phrase "specific combinations of the criteria" should be deleted.

In column 18, line 45, the phrase --specific combinations of the criteria-- should be inserted after the word "fulfill".

In column 21, line 10, the word "ted" should be replaced by the word --fed--.

In column 20, line 67, the word --same-- should appear after the word "substantially".

Signed and Sealed this

Twenty-second Day of August, 1995

Attest:

BRUCE LEHMAN

Attesting Officer

Commissioner of Patents and Trademarks